United States Patent
Wang et al.

(10) Patent No.: US 8,478,536 B2
(45) Date of Patent: *Jul. 2, 2013

(54) METHOD FOR DETERMINING THE CONCENTRATION OF BLOOD GLUCOSE

(75) Inventors: Kuo-Jeng Wang, Kaohsiung (TW); Jian-Tsz Chen, Taichung (TW)

(73) Assignee: Transpacific Systems, LLC, Wilmington, DE (US)

( * ) Notice: Subject to any disclaimer, the term of this patent is extended or adjusted under 35 U.S.C. 154(b) by 1407 days.

This patent is subject to a terminal disclaimer.

(21) Appl. No.: 11/695,967

(22) Filed: Apr. 3, 2007

(65) Prior Publication Data

US 2007/0225583 A1    Sep. 27, 2007

Related U.S. Application Data

(63) Continuation of application No. 10/410,292, filed on Apr. 10, 2003, now Pat. No. 7,222,024.

(30) Foreign Application Priority Data

Dec. 31, 2002   (TW) .............................. 91138108 A

(51) Int. Cl.
 *G01N 33/48* (2006.01)
 *G01N 31/00* (2006.01)
 *G06G 7/48* (2006.01)
 *G06G 7/58* (2006.01)

(52) U.S. Cl.
 USPC ................... 702/19; 702/22; 703/11; 703/12

(58) Field of Classification Search
 None
 See application file for complete search history.

(56) References Cited

U.S. PATENT DOCUMENTS

| | | | |
|---|---|---|---|
| 3,837,922 A | 9/1974 | Ng et al. | |
| 4,005,002 A | 1/1977 | Racine et al. | |
| 4,129,478 A | 12/1978 | Racine et al. | |
| 4,274,832 A | 6/1981 | Wu et al. | |
| 4,299,493 A | 11/1981 | Harrison | |
| 4,407,290 A | 10/1983 | Wilber | |
| 4,407,959 A | 10/1983 | Tsuji et al. | |
| 4,420,564 A | 12/1983 | Tsuji et al. | |
| 4,444,743 A | 4/1984 | Yokoyama et al. | |
| 4,689,309 A * | 8/1987 | Jones | 436/95 |
| 4,731,726 A | 3/1988 | Allen, III | |

(Continued)

FOREIGN PATENT DOCUMENTS

DE      1422172      1/1972
JP      61020680     1/1986

(Continued)

OTHER PUBLICATIONS

Pilosof et al. (Analytical Chemistry, 1982, 54, 1698-1701).*

(Continued)

*Primary Examiner* — Larry D Riggs, II
(74) *Attorney, Agent, or Firm* — Stolowitz Ford Cowger LLP

(57) ABSTRACT

The present invention provides a method for determining concentration of blood glucose by using the change in the rising time. The chemical reaction between the blood glucose and enzyme within the test strip to generate the analog source that used to determine the concentration of the blood glucose in the measuring meter. Thus, the rising curve can be obtained after the analog source is treated, such that the concentration of the blood glucose can be determined.

19 Claims, 4 Drawing Sheets

U.S. PATENT DOCUMENTS

| | | | |
|---|---|---|---|
| 4,772,561 A | 9/1988 | Genshaw | |
| 4,791,066 A | 12/1988 | Ishiguro | |
| 4,805,624 A | 2/1989 | Yao et al. | |
| 4,850,805 A | 7/1989 | Madsen et al. | |
| 4,861,771 A | 8/1989 | Gaitanopoulos et al. | |
| 4,875,486 A | 10/1989 | Rapoport et al. | |
| 4,891,104 A | 1/1990 | Liston et al. | |
| 5,002,893 A | 3/1991 | Rosenthal | |
| 5,198,367 A | 3/1993 | Aizawa et al. | |
| 5,222,495 A | 6/1993 | Clarke et al. | |
| 5,222,496 A | 6/1993 | Clarke et al. | |
| 5,246,002 A | 9/1993 | Prosser | |
| 5,284,845 A | 2/1994 | Paulsen | |
| 5,332,803 A | 7/1994 | Miyazaki et al. | |
| 5,337,745 A | 8/1994 | Benaron | |
| 5,341,805 A | 8/1994 | Stavridi et al. | |
| 5,344,832 A | 9/1994 | Cincotta et al. | |
| 5,362,966 A | 11/1994 | Rosenthal et al. | |
| 5,365,066 A | 11/1994 | Krueger, Jr. et al. | |
| 5,370,114 A | 12/1994 | Wong et al. | |
| 5,407,545 A | 4/1995 | Hirose | |
| 5,420,108 A | 5/1995 | Shohet | |
| 5,468,755 A | 11/1995 | Cincotta et al. | |
| 5,494,562 A | 2/1996 | Maley et al. | |
| 5,496,803 A | 3/1996 | Meier et al. | |
| 5,500,374 A | 3/1996 | Wenzhi | |
| 5,532,602 A | 7/1996 | Wiget | |
| 5,554,623 A | 9/1996 | Cincotta et al. | |
| 5,585,347 A | 12/1996 | Meier et al. | |
| 5,592,086 A | 1/1997 | Weinstock et al. | |
| 5,616,558 A | 4/1997 | Ohneda et al. | |
| 5,666,956 A | 9/1997 | Buchert | |
| 5,700,776 A | 12/1997 | Ohneda et al. | |
| 5,772,586 A | 6/1998 | Heinonen et al. | |
| 5,814,600 A | 9/1998 | Rink et al. | |
| 5,882,935 A | 3/1999 | Hirai et al. | |
| 5,899,855 A | 5/1999 | Brown | |
| 5,997,476 A | 12/1999 | Brown | |
| 6,011,984 A | 1/2000 | Van Antwerp et al. | |
| 6,024,488 A | 2/2000 | Wu et al. | |
| 6,024,699 A | 2/2000 | Surwit et al. | |
| 6,091,976 A | 7/2000 | Pfeiffer et al. | |
| 6,246,992 B1 | 6/2001 | Brown | |
| 6,312,924 B1 | 11/2001 | Presnell et al. | |
| 6,317,700 B1 | 11/2001 | Bagne | |
| 6,350,431 B1 | 2/2002 | Snow et al. | |
| 6,355,788 B1 | 3/2002 | Conklin et al. | |
| 6,361,985 B1 | 3/2002 | Conklin et al. | |
| 6,379,301 B1 | 4/2002 | Worthington et al. | |
| 6,416,988 B1 | 7/2002 | Conklin et al. | |
| 6,428,704 B1 | 8/2002 | Setoguchi et al. | |
| 6,434,409 B1 | 8/2002 | Pfeiffer et al. | |
| 6,558,351 B1 * | 5/2003 | Steil et al. | 604/131 |
| 6,560,471 B1 * | 5/2003 | Heller et al. | 600/347 |
| 6,616,819 B1 | 9/2003 | Liamos | |
| 6,641,533 B2 | 11/2003 | Causey, III et al. | |
| 6,749,740 B2 | 6/2004 | Liamos et al. | |
| 6,942,518 B2 | 9/2005 | Liamos | |
| 7,089,122 B2 | 8/2006 | Huang et al. | |
| 7,347,925 B2 | 3/2008 | Hsieh | |
| 2002/0133064 A1 | 9/2002 | Ueno et al. | |
| 2003/0150724 A1 | 8/2003 | Kawanaka et al. | |
| 2004/0126832 A1 | 7/2004 | Wang et al. | |
| 2004/0210401 A1 | 10/2004 | Huang et al. | |
| 2005/0235345 A1 | 10/2005 | Mitchell | |

FOREIGN PATENT DOCUMENTS

| | | |
|---|---|---|
| JP | 2000060803 | 2/2000 |
| TW | 357517 | 5/1999 |
| TW | 091138108 | 12/2002 |
| WO | WO 0011205 | 3/2000 |

OTHER PUBLICATIONS

Uhegbu et al. (Analytical Chemistry, 1993, 65, 2443-2451).*
Life Scan One Touch Blood Glucose Monitoring System, Owner's Manual, www.lifescan.com/company/about/lsbkgrndr, 79 pages, Oct. 12, 2005.
Boland, Elizabeth et al., Limitations of Conventional Methods of Self-Monitoring of Blood Glucose, Diabetes Care, vol. 24, No. 11, pp. 1858-1862, Nov. 2001.
Gowenlock, Alan et al., Varley's Practical Clinical Biochemestry, pp. 320-332, 1988.
File History of U.S. Appl. No. 10/771,333; filed Feb. 5, 2004.
File History of U.S. Appl. No. 11/501,479; filed Aug. 8, 2006.
File History of U.S. Appl. No. 10/316,049; filed Dec. 11, 2002.
File History of U.S. Appl. No. 11/468,968; filed Aug. 31, 2006.
File History of U.S. Appl. No. 11/469,402; filed Aug. 31, 2006.
File History of U.S. Appl. No. 10/410,292; filed May 10, 2003.
Stolowitz Ford Cowger LLP; Related Case Listing; Sep. 13, 2010; 1 Page.
English Abstract JP Application 61020680; Publication No. 62177445; Aug. 4, 1987; 1 Page.

* cited by examiner

METHOD FOR DETERMINING THE CONCENTRATION OF BLOOD GLUCOSE

CROSS-REFERENCE TO RELATED APPLICATIONS

The present application is a continuation of U.S. application Ser. No. 10/410,292 filed Apr. 10, 2003, now U.S. Pat. No. 7,222,024, which claims priority from Taiwan Patent Application No. 091138108 filed Dec. 31, 2002.

BACKGROUND

1. Field

The present invention generally relates to a method for determining the concentration of blood glucose, and more particularly to a method for determining the concentration of blood glucose by using the change in rising curve.

2. Description of the Prior Art

In the past, many systems have been developed for monitoring blood characteristics. For example, devices have been developed which are capable of determining such blood characteristics as blood oxygenation, glucose concentration, and other blood characteristics. However, significant difficulties have been encountered when attempting to determine blood glucose concentration accurately using noninvasive blood monitoring systems such as by means of spectroscopic measurement.

The difficulty in determining blood glucose concentration accurately may be attributed to several causes. One of the significant causes is that blood glucose is typically found in very low concentrations within the bloodstream (e.g., on the order of 100 to 1,000 times lower than hemoglobin) so that such low concentrations are difficult to detect noninvasively, and require a very high signal-to noise ratio. Additionally, with spectroscopic methods, the optical characteristics of glucose are very similar to those of water, which is found in a very high concentration within the blood. Thus where optical monitoring systems are used, the optical characteristics of water tend to obscure the characteristics of optical signal due to glucose within the bloodstream. Furthermore, since each individual has tissue, bone, and unique blood properties, each measurement typically requires calibration for the particular individual.

Test strips are known that contain a testing reagent that turns a different shade of color, depending on the concentration of glucose in a blood sample that has been applied to the strip. The blood glucose concentration is measured by inserting a strip into a meter that is basically a reflectance photometer, which determines the concentration from the change in color caused by the reaction between the testing reagent and blood glucose. The testing reagent typically contains an enzyme, such as glucose oxidase, which is capable of oxidizing glucose to gluconic acid lactone and hydrogen peroxide; and oxidizable dye; and a substance having peroxidative activity, which is capable of selectively catalyzing oxidation of the oxidizable dye in the presence of hydrogen peroxide.

In the conventional measuring meter, the measuring time is usually of about 10 to 30 seconds which is too long to obtain an exact concentration of the blood glucose, when the concentration of the blood glucose is determined by sampling the data that is basically a fixed sampling time.

BRIEF DESCRIPTION OF THE DRAWINGS

Subject matter is particularly pointed out and distinctly claimed in the concluding portions of the specification. The claimed subject matter, however, both as to organization and the method of operation, together with objects, features and advantages thereof, may be best understood by a reference to the following detailed description when read with the accompanying drawings in which:

DETAILED DESCRIPTION OF THE PREFERRED EMBODIMENT

Some sample embodiments of the invention will now be described in greater detail. Nevertheless, it should be recognized that the present invention can be practiced in a wide range of other embodiments besides those explicitly described, and the scope of the present invention is expressly not limited except as specified in the accompanying claims.

According to the conventional determining method, the time to determine the concentration of blood glucose is of about 10 to 30 seconds, that is too long to increase the inaccuracy in concentration estimation. Thus, the present invention provides a method for determining the concentration of blood glucose by utilizing the rising curve to estimate the exact the concentration.

Figure 1:
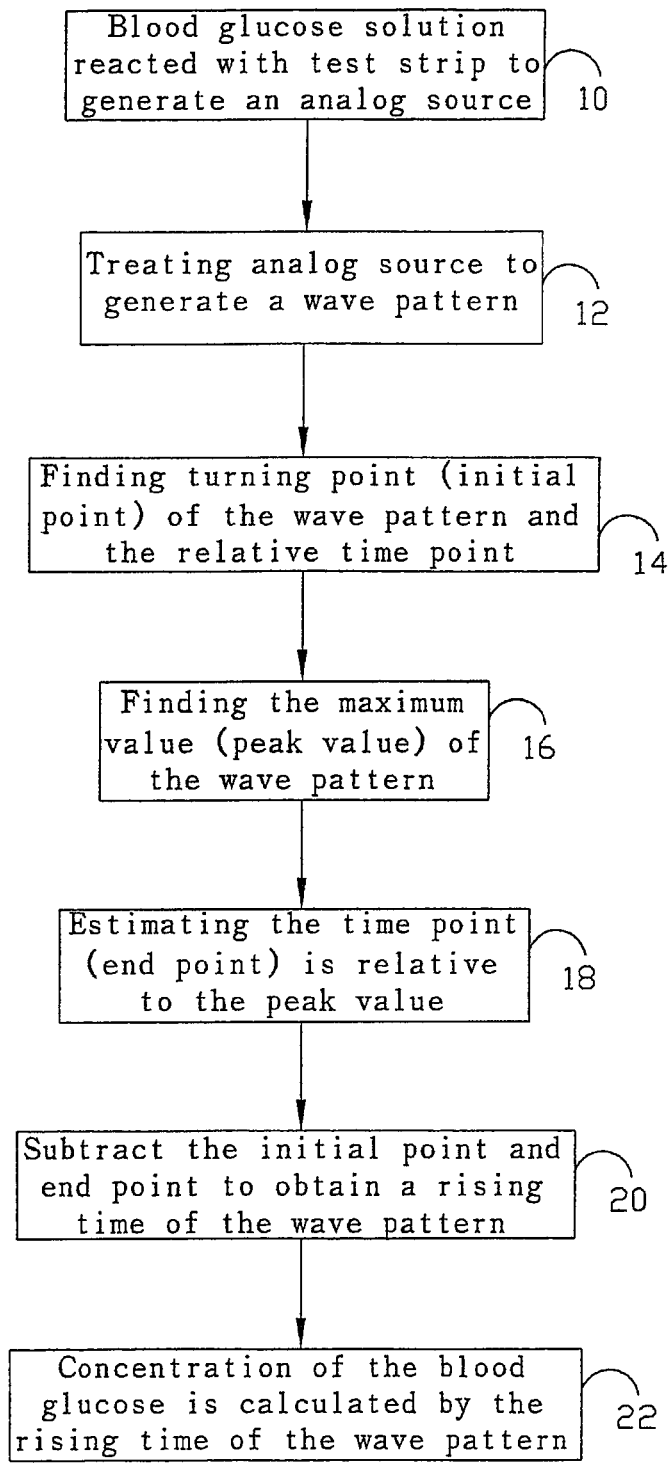
FIG. 1 is a flow chart showing the step for determining the concentration of the blood glucose immediately in accordance with a method disclosed herein.

Referring to FIG. 1, FIG. 1 is a flow chart showing the steps for determining the concentration of the blood glucose by using the rising curve. Step 10 indicates the blood glucose may react with the enzyme within the test strip to generate the analog source; step 12 indicates the treatment device may be used to treat the analog source to convert the analog source from the analog signal into the digital signal, and that the wave pattern is displayed by an outputting device, wherein the wave pattern represents the relationship between the concentration of the blood glucose and rising time. In accordance with the present invention, the outputted signal is represented by voltage; wherein the unit of the voltage is milli-volt (mv.)

Then, the turning point is found from the wave pattern, and the time can be found which is relative to the turning point, wherein the turning point may be named the initial point (step 14.) Next, the maximum value is found from the wave pattern, wherein the maximum value of the wave pattern is the peak value (step 16.) Thereafter, the time point relative to the peak value of the wave pattern can be estimated, wherein the time point relative to the peak value is end point (step 18;) next, the difference value between the initial point and the end point is estimated by subtracting the initial point and the end point, wherein the difference value is the rising time (step 20;) and finally, a relative diagram is constructed by the concentration of the blood glucose and the rising time. Therefore, when the unknown concentration of the blood glucose is inserted into the measuring meter, the concentration of the blood glucose can be obtained immediately from the relative diagram (step 22.)

Figure 2:
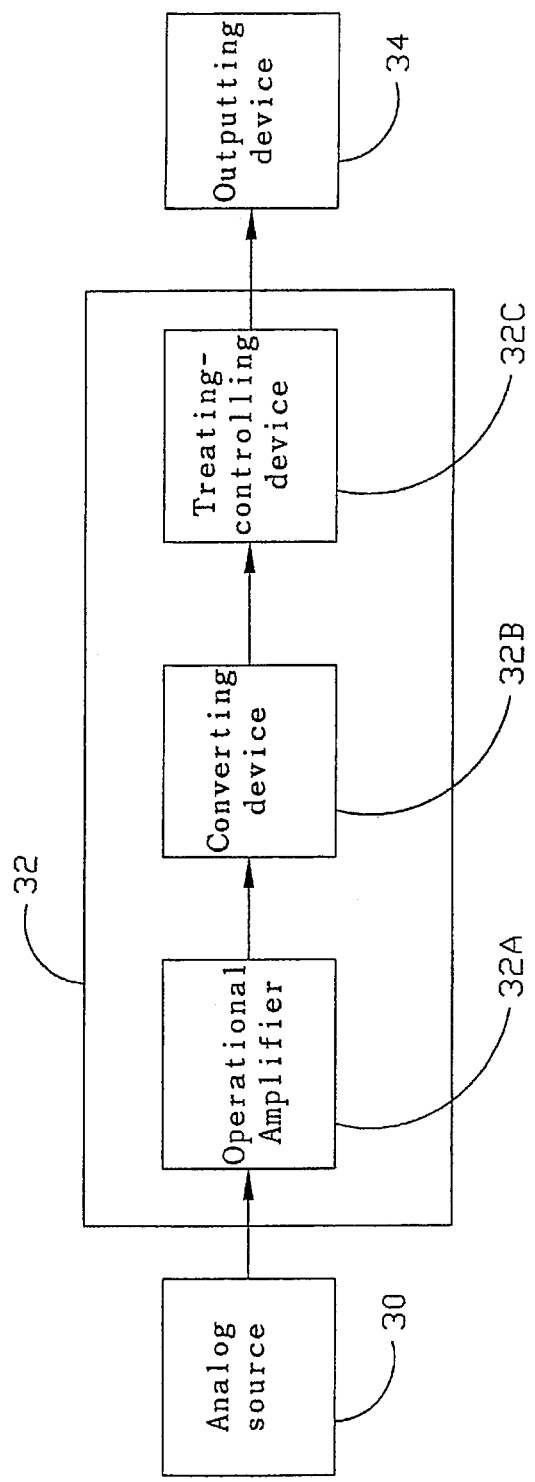
FIG. 2 is a block diagram showing the step for determining the concentration of the blood glucose by using the rising curve in accordance with a method disclosed herein.

Furthermore, FIG. 2 is a block diagram showing the steps for determining the concentration of the blood glucose. The reference character 30 denotes the analog source, wherein the analog source is generated by the chemical reaction between the blood glucose and the enzyme within the test strip, and the chemical reaction is an oxidation-reduction reaction. Then, the analog source is inputted into a treatment device 32 to convert the analog source from the analog signal into a digital signal. The treatment device 32 comprises an operational amplifier 32A, a converting device 32B, and a treating-controlling device 32C. The operational amplifier 32A may be used to transfer the analog signal into the converting device 32B, and the converting device 32B may convert the analog signal into the digital signal, wherein the converting device 32B can be an AFE (analog-front-end) device or ADC (analog-to-digital converting system), and the treating-controlling device 32C is a MCU (microprocessor control unit). Then, the digital signal is displayed by a wave pattern shape in an outputting device 34.

Figure 3:
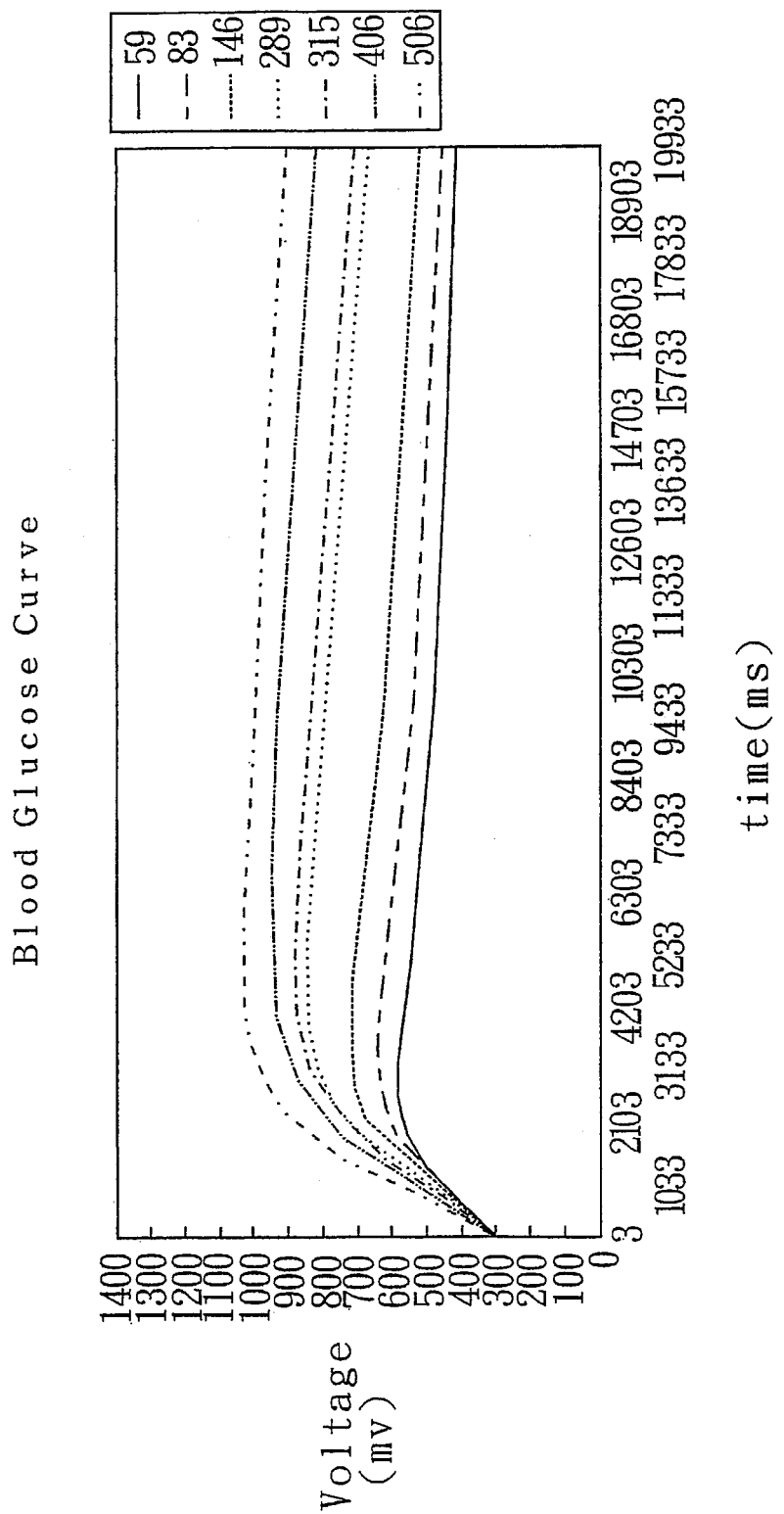
FIG. 3 is schematic representation showing the wave pattern for different concentration of the blood glucose that after treatment in accordance with a method disclosed herein.

Then, the FIG. 3 shows a wave pattern for the different concentration of the blood glucose and the reaction time, wherein the x-coordinate is reaction time, the unit is millisecond (ms), and the y-coordinate is outputted voltage, the unit is milli-volt (mv). Thus, the reaction time of the rising curve will become longer when the blood glucose has a higher concentration, so that the concentration of the blood glucose can be determined by the reaction time of the rising curve.

The preferred embodiment of the present invention provides a method to estimate the different concentration of the blood glucose. First, the turning point of the rising curve can be found, and the time point relative to the turning point of the rising curve also can be found, wherein the turning point is an initial point or first time. Then, according to the value of the first order differential that is greater than the zero, the maximum value of the each concentration of the blood glucose can be found, and the time point relative to the maximum value also can be found, herein the time point is the end point or second time. Next, the difference value between the initial point and end point is estimated by subtracting the initial point and the end point, wherein the difference value is the rising time of the rising curve.

In accordance with the present invention, the rising time is very short and could determine the concentration of the blood glucose immediately. Therefore, the exact concentration value can be estimated by the change in the rising time. To compare the estimating time between the conventional measuring meter and the rising time of the present invention, this invention only needs about 5 seconds to obtain the exact concentration of the blood glucose, nevertheless, the conventional measuring meter requires more than 10 seconds to obtain the concentration of blood glucose.

Figure 4:
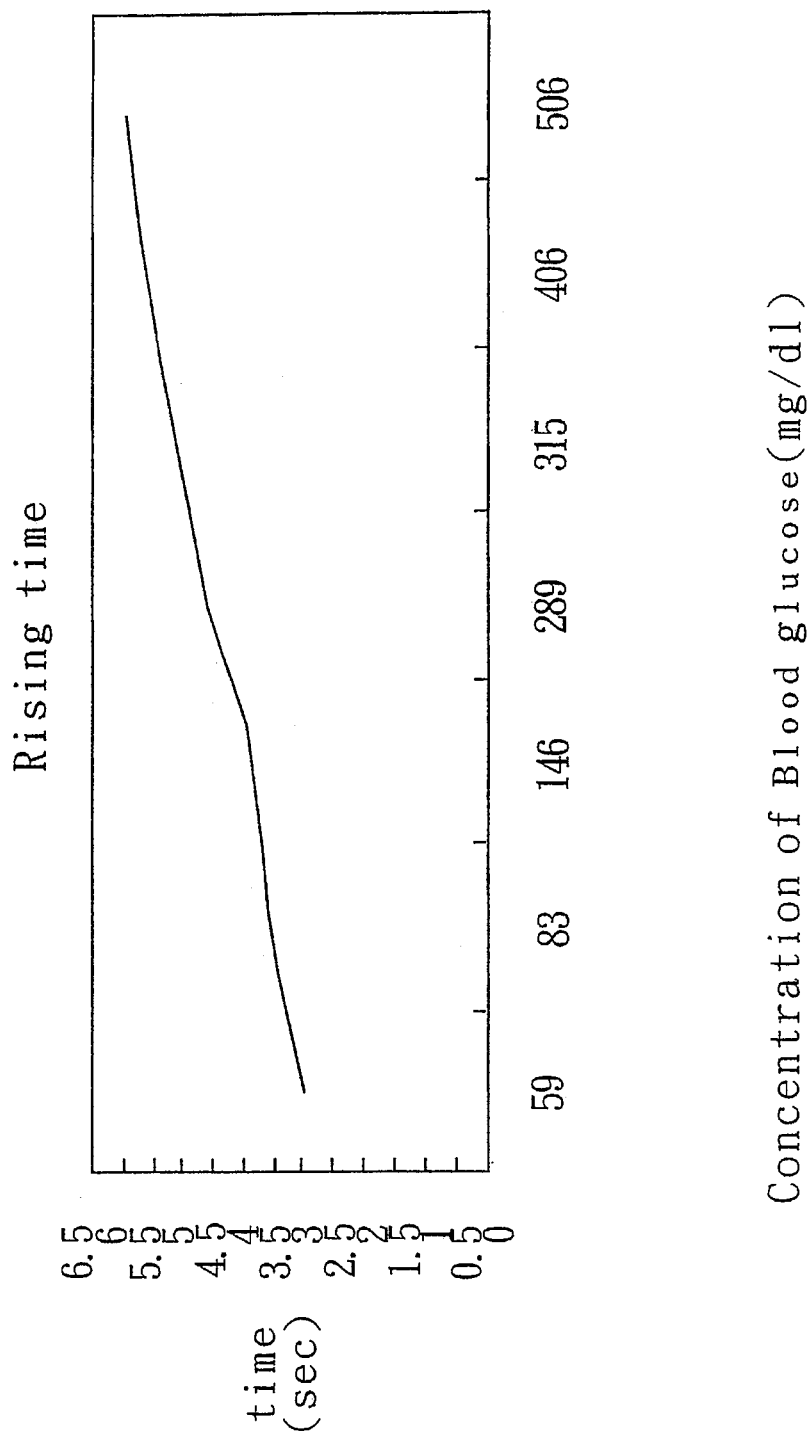
FIG. 4 is a schematic representation showing the relative diagram between the rising time and concentration of the blood glucose.

FIG. 4 is a relative diagram between the different concentration of the blood glucose and the rising time, wherein the x-coordinate is rising time, and the y-coordinate is voltage that expresses the concentration of the blood glucose. Thus, the unknown concentration of the blood glucose can be estimated by the relative diagram.

Although specific embodiments have been illustrated and described, it will be clear to those skilled in the art that various modifications may be made without departing from what is intended to be limited solely by the appended claims.

The following is claimed:

1. A measuring circuit, comprising:
   an amplifier configured to receive an analog signal generated by detection of a product of an oxidation-reduction reaction associated with a concentration of blood glucose on a test strip;
   an analog-to-digital conversion device configured to convert the analog signal into a digital signal; and
   a processing device configured to execute instructions that cause the processing device to perform operations comprising:
      converting the digital signal into a wave pattern;
      identifying a first time and a second time based, at least in part, on the wave pattern, wherein the first time is a turning point of the wave pattern and the second time is a peak value of the wave pattern;
      calculating a time difference value between the first time and the second time, wherein the time difference value corresponds with a rising time; and
      determining the concentration of blood glucose according to the rising time.

2. The measuring circuit of claim 1, wherein:
   the analog signal is generated by detection of the product of a chemical reaction between an enzyme and the concentration of blood glucose;
   the rising time is a reaction time between the enzyme and the concentration of blood glucose; and
   the processing device is further configured to execute the instructions to cause the processing device to perform operations further comprising generating a larger measured value for the concentration of blood glucose when the reaction time is longer and generate a smaller measured value for the concentration of blood glucose when the reaction time is shorter.

3. An apparatus, comprising:
   a conversion device configured to generate an electrical signal corresponding to a product of an oxidation-reduction reaction associated with a concentration of blood glucose on a test strip; and
   a processing device configured to execute instructions that cause the processing device to perform operations comprising:
      converting the electrical signal into a wave pattern;
      calculating a rise time associated with the wave pattern, wherein the rise time corresponds to a difference between an initial time and a second time, and wherein the second time corresponds approximately to a peak value of the electrical signal; and
      correlating a concentration of blood glucose with the rise time.

4. The apparatus of claim 3, wherein the processing device comprises a microprocessor-controlling unit.

5. The apparatus of claim 3, wherein the test strip comprises an enzyme.

6. The apparatus of claim 3, further comprising a display configured to display the concentration of blood glucose.

7. The apparatus of claim 3, wherein the initial time is associated with an initial turning point of the electrical signal.

8. The apparatus of claim 3, wherein the conversion device comprises an amplifier configured to amplify the electrical signal.

9. The apparatus of claim 3, wherein the processing device is further configured to execute the instructions to cause the processing device to perform operations further comprising calculating the rise time, at least in part, according to the wave pattern.

10. An apparatus, comprising:
    a detection device configured to generate a signal corresponding to a product of an oxidation-reduction reaction associated with a concentration of blood glucose on a test strip; and
    a processing device configured to execute instructions that cause the processing device to perform operations comprising:
       converting the signal into a wave pattern;

calculating a rise time associated, at least in part, with the wave pattern, wherein the rise time corresponds to a difference between a first time associated with a turning point of the wave pattern and a second time associated with a peak value of the wave pattern; and determining the concentration of blood glucose according to the rise time.

11. A method, comprising:

generating a signal corresponding to detection of a product an oxidation-reduction reaction associated with a concentration of blood glucose on a test strip;

calculating a rise time of the signal with a treatment device, wherein the rise time corresponds to a difference between an initial time of the signal and a peak time corresponding approximately to a largest value of the signal; and correlating with the treatment device a concentration of blood glucose according to the rise time.

12. The method of claim 11, further comprising:

generating a wave pattern from the signal that identifies the initial time and the peak time; and correlating the concentration of blood glucose according to the wave pattern.

13. The method of claim 11, further comprising calculating a first order differential from the signal to identify the largest value of the signal.

14. The method of claim 11, further comprising using a look-up table to correlate the concentration of blood glucose.

15. The method of claim 11, wherein the initial time is associated with a turning point of the signal.

16. A method, comprising:

generating an electrical signal with an input device, wherein the electrical signal corresponds to a product of an oxidation-reduction reaction associated with blood glucose on a test strip;

generating a wave pattern according to the electrical signal;

identifying a first time associated with a turning value in the wave pattern;

identifying a second time associated with a second substantially plateaued value in the wave pattern; and calculating a blood glucose level according to a difference between the first time and the second time.

17. The method of claim 16, wherein the second substantially plateaued value is substantially a peak value of the wave pattern.

18. The method of claim 16, further comprising using a look-up table to map the difference between the first time and the second time to the blood glucose level.

19. The measuring circuit of claim 1, wherein the test strip comprises an enzyme.

* * * * *